(12) United States Patent
Noh et al.

(10) Patent No.: US 11,248,211 B2
(45) Date of Patent: Feb. 15, 2022

(54) PRIMED CELL THERAPY

(75) Inventors: Moon Jong Noh, Rockville, MD (US); Youngsuk Yi, Rockville, MD (US); Kwan Hee Lee, Rockville, MD (US)

(73) Assignee: KOLON TISSUEGENE, INC., Rockville, MD (US)

(*) Notice: Subject to any disclaimer, the term of this patent is extended or adjusted under 35 U.S.C. 154(b) by 0 days.

(21) Appl. No.: 12/626,567

(22) Filed: Nov. 25, 2009

(65) Prior Publication Data

US 2010/0316612 A1    Dec. 16, 2010

Related U.S. Application Data

(60) Provisional application No. 61/117,881, filed on Nov. 25, 2008.

(51) Int. Cl.
*C12N 5/077* (2010.01)
*A61K 35/12* (2015.01)

(52) U.S. Cl.
CPC ............ *C12N 5/0655* (2013.01); *A61K 35/12* (2013.01); *C12N 2501/115* (2013.01); *C12N 2501/15* (2013.01); *C12N 2501/155* (2013.01)

(58) Field of Classification Search
None
See application file for complete search history.

(56) References Cited

U.S. PATENT DOCUMENTS

| | | | |
|---|---|---|---|
| 5,919,702 A | 7/1999 | Purchio et al. | |
| 6,150,163 A | 11/2000 | McPherson et al. | |
| 6,835,377 B2* | 12/2004 | Goldberg et al. | 424/93.7 |
| 7,169,610 B2* | 1/2007 | Brown | 435/404 |
| 7,273,756 B2* | 9/2007 | Adkisson et al. | 435/375 |
| 2003/0185809 A1 | 10/2003 | Song et al. | |
| 2004/0018257 A1* | 1/2004 | Boumediene et al. | 424/757 |
| 2008/0075703 A1 | 3/2008 | Song et al. | |

OTHER PUBLICATIONS

Brittberg et al. (1994, N. Engl. J. Med. 331: 889-895).*
Table, http://jcem.endojournals.org/content/suppl/2008/03/14/jc.2007-2188.DC1/Supplementary_Table_2.pdf accessed on Jan. 31, 2013.*
TGF-beta superfamily, http://www.rndsystems.com/molecule_group.aspx?g=687&r=7, accessed Jul. 10, 2013.*
The TGF-beta superfamily, http://www.rndsystems.com/cb_detail_objectname_wi07_tgf-b_superfamily.aspx, accessed Jul. 10, 2013.*
Revell et al. (2009, Tissue Engineering 15:1-16).*
Wakitani et al. (2008, J Bone Miner Metab 26:115-122).*
Jakob, M., et al. "Specific Growth Factors During the Expansion and Redifferentiation of Adult Human Articular Chondrocytes Enhance Chondrogenesis and Cartilaginous Tissue Formation in Vitro," Journal of Cellular Biochemistry, vol. 81, 2001, pp. 368-377.
Lee, Jong Eun, et al., "Effects of the controlled-released TGF-β1 from chitosan microspheres on chondrocytes cultured in a collagen/chitosan/glycosaminoglycan scaffold," Biomaterials, vol. 25, 2004, pp. 4163-4173.
Miura, Masako, et al., "Thyroid Hormones Promote Chondrocyte Differentiation in Mouse ATDC5 Cells and Stimulate Endochondral Ossification in Fetal Mouse Tibias Through Iodothyronine Deiodinases in the Growth Plate," Journal of Bone and Mineral Research, vol. 17, No. 3, 2002, pp. 443-454.
Okazaki, Ryuji, et al., "Effects of transforming growth factor βs and basic fibroblast growth factor on articular chondrocytes obtained from immobilised rabbit knees," Annals of Rheumatic Diseases, vol. 55, 1996, pp. 181-186.
Song, Sun U., et al., "Hyaline Cartilage Regeneration Using Mixed Human Chondrocytes and Transforming Growth Factor-β1-Producing Chondrocytes," Tissue Engineering, vol. 11, No. 9/10, 2005, pp. 1516-1526.
Zimber, Michael P., et al., "TGF-β Promotes the Growth of Bovine Chondrocytes in Monolayer Culture and the Formation of Cartilage Tissue on Three-Dimensional Scaffolds," Tissue Engineering, vol. 1, No. 3, 1995, pp. 289-300.
Examination Report No. 2 dated Apr. 16, 2020, issued in Australian Patent Application No. 2018203611, 4 pages.
Notice of Preliminary Rejection dated Jun. 15, 2020, issued in Korean Patent Application No. 10-2019-7019444, 17 pages.

\* cited by examiner

*Primary Examiner* — Elizabeth C. Kemmerer
(74) *Attorney, Agent, or Firm* — Fisherbroyles, LLP

(57) ABSTRACT

The subject invention is directed to a composition comprising primed connective tissue cells and a pharmaceutically acceptable carrier thereof.

24 Claims, 6 Drawing Sheets

Specification includes a Sequence Listing.

PRIMED CELL THERAPY

CROSS-REFERENCE TO RELATED APPLICATIONS

The present application claims the benefit of priority to U.S. Provisional Patent Application No. 61/117,881, filed Nov. 25, 2008, the disclosure of which is hereby incorporated by reference in its entirety.

BACKGROUND OF THE INVENTION

Field of the Invention

The present invention relates to using cells primed by incubation with a cytokine for somatic cell therapy.

Brief Description of the Related Art

In the orthopedic field, degenerative arthritis or osteoarthritis is the most frequently encountered disease associated with cartilage damage. Almost every joint in the body, such as the knee, the hip, the shoulder, and even the wrist, is affected. The pathogenesis of this disease is the degeneration of hyaline articular cartilage (Mankin et al., J Bone Joint Surg, 52A: 460-466, 1982). The hyaline cartilage of the joint becomes deformed, fibrillated, and eventually excavated. If the degenerated cartilage could somehow be regenerated, most patients would be able to enjoy their lives without debilitating pain.

Traditional routes of drug delivery, such as oral, intravenous or intramuscular administration, to carry the drug to the joint are inefficient. The half-life of drugs injected intra-articularly is generally short. Another disadvantage of intra-articular injection of drugs is that frequent repeated injections are necessary to obtain acceptable drug levels at the joint spaces for treating a chronic condition such as arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as gastrointestinal upset and changes in the hematological, cardiovascular, hepatic and renal systems of the mammalian host.

In the orthopedic field, some cytokines have been considered as candidates for the treatment of orthopedic diseases. Bone morphogenic protein has been considered to be an effective stimulator of bone formation (Ozkaynak et al., EMBO J, 9:2085-2093, 1990; Sampath and Rueger, Complications in Ortho, 101-107, 1994), and TGF-β has been reported as a stimulator of osteogenesis and chondrogenesis (Joyce et al., J Cell Biology, 110:2195-2207, 1990).

Transforming growth factor-β (TGF-β) is considered to be a multifunctional cytokine (Sporn and Roberts, Nature (London), 332: 217-219, 1988), and plays a regulatory role in cellular growth, differentiation and extracellular matrix protein synthesis (Madri et al., J Cell Biology, 106: 1375-1384, 1988). TGF-β inhibits the growth of epithelial cells and osteoclast-like cells in vitro (Chenu et al., Proc Natl Acad Sci, 85: 5683-5687, 1988), but it stimulates enchondral ossification and eventually bone formation in vivo (Critchlow et al., Bone, 521-527, 1995; Lind et al., A Orthop Scand, 64(5): 553-556, 1993; and Matsumoto et al., In vivo, 8: 215-220, 1994). TGF-β-induced bone formation is mediated by its stimulation of the subperiosteal pluripotential cells, which eventually differentiate into cartilage-forming cells (Joyce et al., J Cell Biology, 110: 2195-2207, 1990; and Miettinen et al., J Cell Biology, 127-6: 2021-2036, 1994).

The biological effect of TGF-β in orthopedics has been reported (Andrew et al., Calcif Tissue In. 52: 74-78, 1993; Borque et al., Int J Dev Biol., 37:573-579, 1993; Carrington et al., J Cell Biology, 107:1969-1975, 1988; Lind et al., A Orthop Scand. 64(5):553-556, 1993; Matsumoto et al., In vivo, 8:215-220, 1994). In mouse embryos, staining shows that TGF-β is closely associated with tissues derived from the mesenchyme, such as connective tissue, cartilage and bone. In addition to embryologic findings, TGF-β is present at the site of bone formation and cartilage formation. It can also enhance fracture healing in rabbit tibiae. Recently, the therapeutic value of TGF-β has been reported (Critchlow et al., Bone, 521-527, 1995; and Lind et al., A Orthop Scand, 64(5): 553-556, 1993), but its short-term effects and high cost have limited wide clinical application.

During their multiplication in culture through repeated passaging, chondrocytes inevitably lose their ability to produce cartilaginous matrix such as glycosaminoglycan (GAG) and type II collagen (COL2) and begin producing type I collagen (COL1), which is called dedifferentiation. It has long been known that human articular chondrocytes can undergo only a limited number of cell divisions in vitro and that their proliferative potential decreases with age.

Applicants have demonstrated that the conditions of expansion of human articular chondrocytes can modulate the cell's ability to re-enter the differentiation program and to increase growth potential in vitro.

U.S. Pat. Nos. 5,858,355 and 5,766,585 disclose making a viral or plasmid construct of the IRAP (interleukin-1 receptor antagonist protein) gene; transfecting synovial cells (U.S. Pat. No. 5,858,355) and bone marrow cells (U.S. Pat. No. 5,766,585) with the construct; and injecting the transfected cells into a rabbit joint, but there is no disclosure of using primed chondrocyte to regenerate connective tissue.

U.S. Pat. Nos. 5,846,931 and 5,700,774 disclose injecting a composition that includes a bone morphogenesis protein (BMP), which belongs to the TGF β "superfamily", together with a truncated parathyroid hormone related peptide to effect the maintenance of cartilaginous tissue formation, and induction of cartilaginous tissue. However, there is no disclosure of a gene therapy method using the BMP gene, nor the use of primed chondrocytes.

U.S. Pat. No. 5,842,477 discloses implanting a combination of a scaffolding, periosteal/perichondrial tissue, and stromal cells, including chondrocytes, to a cartilage defected area. Since this patent disclosure requires that all three of these elements be present in the implanted system, the reference fails to disclose or suggest the simple cell therapy method of the invention which does not require the implantation of the scaffolding or the periosteal/perichondrial tissue.

In spite of these prior art disclosures, there remains a very real and substantial need for a more effective and potent treatment method to not only regenerate connective tissue in the mammalian host, but also better and more effective somatic cell gene therapy methods as well.

SUMMARY OF THE INVENTION

The present invention has met the herein before described need.

In one aspect, the present invention is directed to a cytokine or a combination of cytokines, which induce re-differentiation of chondrocytes that have lost their ability to produce cartilaginous matrix. The invention relates to a cytokine which can facilitate cell growth of primary chondrocyte in vitro. In addition, cartilage tissue may be formed using re-differentiated chondrocyte without employing a three-dimensional matrix. Applicants have also discovered that sequential treatment of cells with the growth and re-differentiation facilitating cytokine maximizes cartilage tissue regeneration.

In one aspect, the present invention is directed to a composition comprising primed connective tissue cells and a pharmaceutically acceptable carrier thereof. The cells may be fibroblasts, chondrocytes or fibroblastic chondrocytes. The cells may be human cells. The cells may be injectable. The cells may be contained in a storage container for storing cells at a temperature of about −70° C. to about −196° C.

In another aspect, the invention is directed to a method of stimulating regeneration of cartilage at a target site in a mammal comprising: (i) incubating a connective tissue cell with a composition comprising cytokine to create a primed cell; (ii) optionally separating the cytokine from the connective tissue cell; and (iii) injecting a therapeutically effective amount of the primed cell into a target joint site where cartilage is desired to be generated, wherein endogenously existing forms of the connective tissue cells are decreased at the target site, and wherein the presence of the primed cells at the target site stimulates regeneration of cartilage. The connective tissue cells may be fibroblasts, chondrocytes or fibroblastic chondrocytes. The chondrocytes may be primary human chondrocytes. The cytokine may be a member belonging to the TGF-β superfamily. The connective cells may be incubated for about 1 hr to about 2 weeks to create the primed cells. The connective cells may be incubated for about 1 hr to about 40 hours to create the primed cells. The cytokine may be TGF-β. The cytokine may be present in an amount of at least 1 ng/ml. The subject may suffer from degenerative arthritis. Or, the target site may be the intervertebral disc in the spine.

In another aspect, the invention is directed to a second population of mammalian cells transfected or transduced with a gene that is sought to be expressed in addition to the primed cells.

In still another aspect, the invention is directed to a mixed cell composition, comprising hyaline cartilage-generating effective amount of: (a) a first population of primed chondrocytes or fibroblast; (b) a second population of fibroblast or chondrocyte cells that have been transfected or transduced with a gene encoding a member of the TGF-β superfamily; and (c) a pharmaceutically acceptable carrier thereof. The gene may be TGF-β1, TGF-β2, TGF-β3, BMP-2, BMP-3, BMP-4, BMP-5, BMP-6, BMP-7 or BMP-9. In this composition, the ratio of the first population of primed cells to the second population of fibroblast or chondrocyte cells that have been transfected or transduced with a gene encoding a member of the TGF-β superfamily may be about 1-20 to 1; from about 1-10 to 1; or from about 1-3 to 1. The second population of cells transfected or transduced with a gene may be irradiated. In the inventive composition, the first population of cells and the second population of cells may be derived from the same source organism or different source organisms.

In yet another aspect, the invention is directed to a method of generating a mixed cell composition comprising: (A) creating a first population of cells comprising the steps of: (i) incubating a connective tissue cell with a composition comprising cytokine to create a first population of primed cells, and (ii) optionally separating the cytokine from the connective tissue cell; (B) creating a second population of cells comprising the steps of: (i) generating a recombinant vector comprising a DNA sequence encoding the therapeutic protein operatively linked to a promoter, (ii) transfecting or transducing a population of cells in vitro with said recombinant vector to create the second population of cells; and (C) mixing the first and second population of cells together to result in the mixed cell composition.

In yet another aspect, the invention is directed to a method of stimulating regeneration of cartilage at a target site in a mammal comprising: (A) creating a first population of cells comprising the steps of: (i) incubating a connective tissue cell with a composition comprising a cytokine to create a first population of primed cells, and (ii) optionally separating the cytokine from the connective tissue cell; (B) creating a second population of cells comprising the steps of: (i) generating a recombinant vector comprising a DNA sequence encoding the therapeutic protein operatively linked to a promoter, (ii) transfecting or transducing a population of cells in vitro with said recombinant vector to create the second population of cells; and (C) injecting a therapeutically effective amount of a mixture of the first and second population of cells into a target joint site where cartilage is desired to be generated, wherein endogenously existing forms of the connective tissue cells are decreased at the target site, and wherein the presence of the mixture of cells at the target site stimulates regeneration of cartilage. In this method, the gene may be TGF-β1, TGF-β2, TGF-β3, BMP-2, BMP-3, BMP-4, BMP-5, BMP-6, or BMP-7. In this method, the first and second population of cells may be syngeneic, allogeneic, or xenogeneic with respect to the host recipient. The recombinant vector may be a viral vector or plasmid. The cells may be stored optionally in a cryopreservative prior to injection.

Yet in another aspect, the invention is directed to a method of treating osteoarthritis comprising: (A) creating a first population of cells comprising the steps of: (i) incubating a connective tissue cell with a composition including cytokine to create a first population of primed cells; and (ii) optionally separating the cytokine from the connective tissue cell; (B) creating a second population of cells comprising the steps of: (i) generating a recombinant vector comprising a DNA sequence encoding the therapeutic protein operatively linked to a promoter; (ii) transfecting or transducing a population of cells in vitro with said recombinant vector to create the second population of cells; and (C) injecting a therapeutically effective amount of a mixture of the first and second population of cells and a pharmaceutically acceptable carrier thereof that is not a non-living three dimensional structure into a joint space of a mammal into a target joint site where cartilage is desired to be generated, wherein endogenously existing forms of the connective tissue cells are decreased at the target site, and wherein the presence of the mixture of cells at the target site stimulates regeneration of cartilage to treat osteoarthritis.

In still another embodiment, the invention is directed to a method of decreasing doubling time of connective tissue cell comprising incubating a connective tissue cell with a composition including a cytokine to create a primed cell. The connective tissue cells may be fibroblasts, chondrocytes or fibroblastic chondrocytes. The chondrocytes may be primary human chondrocytes. The cytokine may be a member belonging to the TGF-β superfamily. The cells may be incubated for about 1 hr to about 2 weeks with the cytokine to create the primed cell. The doubling time may be about half of a control unincubated cell. The cytokine may be a combination of FGF and TGFbeta1. The composition may include 3,3',5-Triiodo-L-thyronine.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE INVENTION

Figure 1:
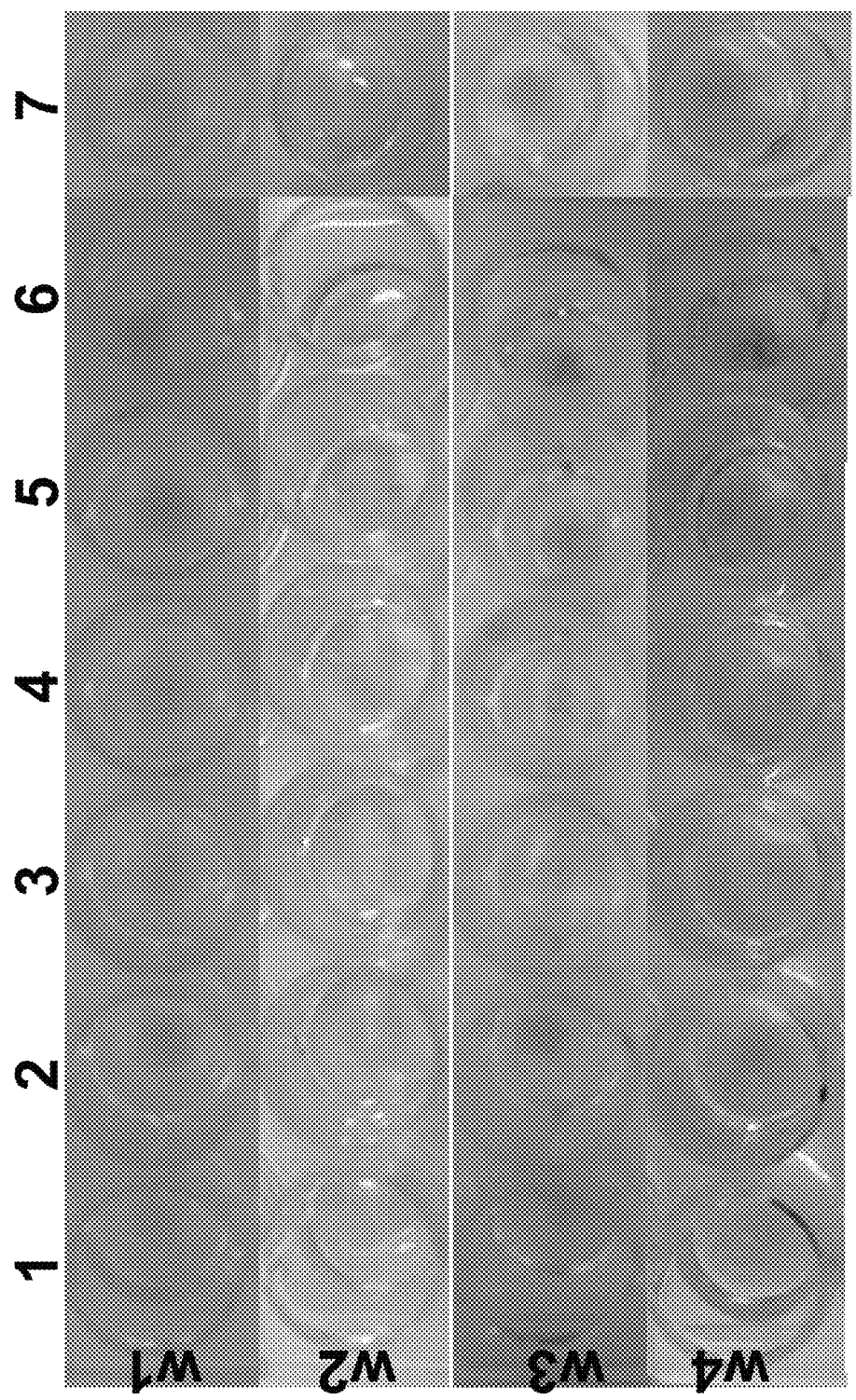
FIG. 1 shows results of Alcian Blue staining of cells at various times (weeks) after incubating fibroblastic chondrocytes with TGFβ1. 1. 18 hr incubation with 10 ng/mL TGFβ1; 2. 18 hr incubation with 50 ng/mL TGFβ1; 3. 6 hr incubation with 10 ng/mL TGFβ1; 4. 6 hr incubation with 50 ng/mL TGFβ1; 5. Incubation with 1 ng/mL TGFβ1; 6. Incubation with 10 ng/mL TGFβ1 without separation out of the cytokine; 7. Untreated control fibroblastic chondrocytes.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "connective tissue" is any tissue that connects and supports other tissues or organs, and includes but is not limited to a ligament, a cartilage, a tendon, a bone, and a synovium of a mammalian host.

As used herein, the terms "connective tissue cell" and "cell of a connective tissue" include cells that are found in the connective tissue, such as fibroblasts, cartilage cells (chondrocytes), and bone cells (osteoblasts/osteocytes), which secrete collagenous extracellular matrix, as well as fat cells (adipocytes) and smooth muscle cells. Preferably, the connective tissue cells are fibroblasts, cartilage cells, and bone cells. It will be recognized that the invention can be practiced with a mixed culture of connective tissue cells, as well as cells of a single type. It is also recognized that the tissue cells may be pretreated with chemical compounds or radiation before injecting them into the joint space so that the cells stably express the gene of interest within the host organism. Preferably, the connective tissue cell does not cause a negative immune response when injected into the host organism. It is understood that allogeneic cells may be used in this regard, as well as autologous cells for cell-mediated gene therapy or somatic cell therapy.

As used herein, "connective tissue cell line" includes a plurality of connective tissue cells originating from a common parent cell.

As used herein, "decrease" of cells refers to a lessening of a population of cells compared with the amount that would normally be found at the site. This may mean a percentage reduction of a population of cells, such as at least 10%, 20%, 30%, 40%, 50%, 60%, 70%, 80%, or 90% compared with the normal cell population at the locus, or may mean damage or depletion of the cells at the locus.

As used herein, "histocompatibility" of a donor cell and recipient host refers to their sharing of a sufficient number of histocompatibility agents so that a transplantation is accepted and remains functional in the host mammal In particular, the donor and recipient pair should be matched for Human Leukocyte Antigens (HLA), such as HLA type A, B, and C (Class I) and HLA type DR (Class II).

As used herein, "hyaline cartilage" refers to the connective tissue covering the joint surface. By way of example only, hyaline cartilage includes, but is not limited to, articular cartilage, costal cartilage, and nose cartilage.

In particular, hyaline cartilage is known to be self-renewing, responds to alterations, and provides stable movement with less friction. Hyaline cartilage found even within the same joint or among joints varies in thickness, cell density, matrix composition and mechanical properties, yet retains the same general structure and function. Some of the functions of hyaline cartilage include surprising stiffness to compression, resilience, and exceptional ability to distribute weight loads, ability to minimize peak stress on subchondral bone, and great durability.

Grossly and histologically, hyaline cartilage appears as a slick, firm surface that resists deformation. The extracellular matrix of the cartilage comprises chondrocytes, but lacks blood vessels, lymphatic vessels or nerves. An elaborate, highly ordered structure that maintains interaction between chondrocytes and the matrix serves to maintain the structure and function of the hyaline cartilage, while maintaining a low level of metabolic activity. The reference O'Driscoll, J. Bone Joint Surg., 80A: 1795-1812, 1998 describes the structure and function of hyaline cartilage in detail, which is incorporated herein by reference in its entirety.

As used herein, "injectable" composition refers to a composition that excludes various three-dimensional scaffold, framework, mesh or felt structure, which may be made of any material or shape that allows cells to attach to it and allows cells to grow in more than one layer, and which structure is generally implanted, and not injected. In one embodiment, the injection method of the invention is typically carried out by a syringe. However, any mode of injecting the composition of interest may be used. For instance, catheters, sprayers, or temperature dependent polymer gels also may be used.

As used herein, the term "mammalian host" includes members of the animal kingdom including but not limited to human beings.

As used herein, "mixed cell" or a "mixture of cells" or "cell mixture" refers to the combination of a plurality of cells that include a population of cells that are transfected or transduced with a gene of interest that is expressed, and at least one other population of cells that includes primed cells.

In one embodiment of the invention, mixed cells may refer to the combination of a plurality of connective tissue cells that include cells that have been transfected or transduced with a gene or DNA encoding a member of the transforming growth factor β superfamily and primed cells that have not been transfected or transduced with a gene encoding a member of the transforming growth factor β superfamily. Typically, the ratio of primed cells that have not been transfected or transduced with a gene encoding a member of the transforming growth factor β superfamily to cells that have been transfected or transduced with a TGF superfamily gene may be in the range of about 3-20 to 1. The range may include about 3-10 to 1. In particular, the range may be about 10 to 1 in terms of the number of cells. However, it is understood that the ratio of these cells should not be necessarily fixed to any particular range so long as the combination of these cells is effective to produce hyaline cartilage in partially and fully defected joints.

As used herein, the term "patient" includes members of the animal kingdom including but not limited to human beings.

As used herein, "pharmaceutically acceptable carrier" refers to any carrier that is known in the art to promote the efficiency of transport of the composition of the invention and prolong the effectiveness of the composition.

As used herein, the term "primed" cell refers to cells that that have been activated or changed to express certain genes.

As used herein, "somatic cell" or "cell" in general refers to the cell of the body other than egg or sperm.

As used herein, "stored" cells refer to a composition of primed cells of a population of mixed cells that include the primed cells that have been either stored individually or together before they are administered to the joint space. The cells may be stored in a refrigeration unit. Alternatively, the cells may be frozen at about −70° to about −196° C. in a liquid nitrogen tank or in an equivalent storage unit so that the cells are preserved for later administration into the joint space. The cells may be thawed using known protocols. The duration of freezing and thawing may be carried out by any number of ways, so long as the viability and potency of the cells are optimized.

As used herein, the terms "transfection" and "transduction" are mentioned as particular methods of transferring the DNA to the host cell and its subsequent integration into the recipient cell's chromosomal DNA. As the invention is practiced, any method of transferring a foreign DNA to a host cell may be used, including nonviral or viral gene transfer methods, so long as a foreign gene is introduced into the host cell and the foreign gene is stably expressed in the host cell. Thus, as used herein, the term "transfected or transduced" includes any method of gene delivery to the cells, such as calcium phosphate precipitation, DEAE dextran, electroporation, liposome, viral mediation and so on.

As used herein, the "transforming growth factor-β (TGF-β) superfamily" encompasses a group of structurally related proteins, which affect a wide range of differentiation processes during embryonic development. The family includes, Müllerian inhibiting substance (MIS), which is required for normal male sex development (Behringer, et al., Nature, 345:167, 1990), *Drosophila decapentaplegic* (DPP) gene product, which is required for dorsal-ventral axis formation and morphogenesis of the imaginal disks (Padgett, et al., Nature, 325:81-84, 1987), the *Xenopus* Vg-1 gene product, which localizes to the vegetal pole of eggs (Weeks, et al., Cell, 51:861-867, 1987), the activins (Mason, et al., Biochem, Biophys. Res. Commun., 135:957-964, 1986), which can induce the formation of mesoderm and anterior structures in *Xenopus* embryos (Thomsen, et al., Cell, 63:485, 1990), and the bone morphogenetic proteins (BMP's, such as BMP-2, 3, 4, 5, 6 and 7, osteogenin, OP-1) which can induce de novo cartilage and bone formation (Sampath, et al., J. Biol. Chem., 265:13198, 1990). The TGF-β gene products can influence a variety of differentiation processes, including adipogenesis, myogenesis, chondrogenesis, hematopoiesis, and epithelial cell differentiation. For a review, see Massague, Cell 49:437, 1987, which is incorporated herein by reference in its entirety.

The proteins of the TGF-β family are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-β's (Cheifetz, et al., Cell, 48:409, 1987), heterodimers have also been detected, and these appear to have different biological properties than the respective homodimers.

Members of the superfamily of TGF-β genes include TGF-β3, TGF-β2, TGF-β4 (chicken), TGF-β1, TGF-β5 (*Xenopus*), BMP-2, BMP-4, *Drosophila* DPP, BMP-5, BMP-6, Vgr1, OP-1/BMP-7, *Drosophila* 60A, GDF-1, *Xenopus* Vgf, BMP-3, Inhibin-β A, Inhibin-βB, Inhibin-α, and MIS. These genes are discussed in Massague, Ann Rev. Biochem. 67:753-791, 1998, which is incorporated herein by reference in its entirety.

Preferably, a member of the superfamily of TGF-β genes is TGF-β or BMP. More preferably, the member is TGF-β1, TGF-β2, TGF-β3, BMP-2, BMP-3, BMP-4, BMP-5, BMP-6, or BMP-7. Most preferably, the member is human or porcine TGF-β1 or BMP-2.

Primed Cell Therapy

The present invention encompasses administering primed cells to a site in need thereof in a mammal to produce collagen or hyaline cartilage. Primed cells are typically connective tissue cells, and include chondrocytes or fibroblasts.

By way of example, when a population of primary chondrocytes are passaged about 3 or 4 times, their morphology typically changes to fibroblastic chondrocytes. As primary chondrocytes are passaged, they begin to lose some of their chondrocytic characteristics and begin to take on the characteristics of fibroblastic chondrocytes. The inventors have discovered that when these fibroblastic chondrocytes are incubated or "primed" with a cytokine such as a protein from the TGF-β superfamily, the cells regain their chondrocytic characteristics, which include production of collagen.

Such primed cells include fibroblastic chondrocytes, which have been incubated with TGFβ1, and as a result have reverted to type II collagen producing chondrocytes. An advantage of using primed cells in the treatment of osteoarthritis or regeneration of cartilage is the ease of creating useable chondrocytes for introduction into joints or other places in the body where cartilage is desired to be generated such as in the intervertebral disc in the spine for production of collagen and otherwise maintenance of the cartilaginous matrix.

The cells may include without limitation primary cells or cells which have undergone about one to twenty passages. The cells may be connective tissue cells. The cells may include cells that have undergone a morphogenic change, wherein the priming causes reversion to the characteristics of the original cell. The cells may include without limitation chondrocytes, fibroblasts, or fibroblastic chondrocytes. Priming may occur by incubating the cells for a period of at least 1 hr, preferably from 1 hr to two weeks; from 1 to 10 days, from 5 to 10 days or 5 to 7 days, with a cytokine, and then optionally separating the cytokine from the cells and injecting the primed cells into a cartilaginous defect site of interest in order to regenerate cartilage, preferably hyaline cartilage. In one aspect, the cytokine may be a member of the superfamily of TGF-β. In particular, the cytokine may be TGF-β, and in particular, TGF-β1.

The cytokine may be present in the incubation mix in an amount of at least about 1 ng/ml, from about 1 to 1000 ng/ml, from about 1 to 750 ng/ml, from about 1 to 500 ng/ml, from about 1 to 400 ng/ml, from about 1 to 300 ng/ml, from about 1 to 250 ng/ml, from about 1 to 200 ng/ml, from about 1 to 150 ng/ml, from about 1 to 100 ng/ml, from about 1 to 75 ng/ml, from about 1 to 50 ng/ml, from about 10 to 500 ng/ml, from about 10 to 400 ng/ml, from about 10 to 300 ng/ml, from about 10 to 250 ng/ml, from about 10 to 200 ng/ml, from about 10 to 150 ng/ml, from about 10 to 100 ng/ml, from about 10 to 75 ng/ml, from about 10 to 50 ng/ml, from about 15 to 500 ng/ml, from about 15 to 400 ng/ml, from about 15 to 300 ng/ml, from about 15 to 250 ng/ml, from about 15 to 200 ng/ml, from about 15 to 150 ng/ml, from about 15 to 100 ng/ml, from about 15 to 75 ng/ml, from about 15 to 50 ng/ml, from about 20 to 500 ng/ml, from about 20 to 400 ng/ml, from about 20 to 300 ng/ml, from about 20 to 250 ng/ml, from about 20 to 200 ng/ml, from about 20 to 150 ng/ml, from about 20 to 100 ng/ml, from about 20 to 75 ng/ml, from about 20 to 50 ng/ml, from about 25 to 500 ng/ml, from about 25 to 400 ng/ml, from about 25 to 300 ng/ml, from about 25 to 250 ng/ml, from about 25 to 200 ng/ml, from about 25 to 150 ng/ml, from about 25 to 100 ng/ml, from about 25 to 75 ng/ml, from about 25 to 50 ng/ml, from about 30 to 500 ng/ml, from about 30 to 400 ng/ml, from about 30 to 300 ng/ml, from about 30 to 250 ng/ml, from about 30 to 200 ng/ml, from about 30 to 150 ng/ml, from about 30 to 100 ng/ml, from about 30 to 75 ng/ml, from about 30 to 50 ng/ml, from about 35 to 500 ng/ml, from about 35 to 400 ng/ml, from about 35 to 300 ng/ml, from about 35 to 250 ng/ml, from about 35 to 200 ng/ml, from about 35 to 150 ng/ml, from about 35 to 100 ng/ml, from about 35 to 75 ng/ml, from about 35 to 50 ng/ml, from about 40 to 500 ng/ml, from about 40 to 400 ng/ml, from about 40 to 300 ng/ml, from about 40 to 250 ng/ml, from about 40 to 200 ng/ml, from about 40 to 150 ng/ml, from about 40 to 100 ng/ml, from about 40 to 75 ng/ml, or from about 40 to 50 ng/ml.

One method of practicing the invention may include incubating the cells with a cytokine for a certain length of time to create primed cells and optionally separating the cytokine from the cells, and injecting the primed cells into the connective tissue defect site of interest. Alternatively, the cells may be incubated with the cytokine of interest for a time and the combination may be administered to the site of connective tissue defect without separating out the cytokine.

It is to be understood that while it is possible that substances such as a scaffolding or a framework as well as various extraneous tissues may be implanted together in the primed cell therapy protocol of the present invention, it is also possible that such scaffolding or tissue not be included in the injection system of the invention. In a preferred embodiment, in the inventive somatic cell therapy, the invention is directed to a simple method of injecting a population of primed connective tissue cells to the joint space.

It will be understood by the artisan of ordinary skill that the source of cells for treating a human patient may be the patient's own connective tissue cells, such as autologous fibroblast or chondrocyte cells, but that allogeneic cells as well as xenogeneic cells may also be used without regard to the histocompatibility of the cells. Alternatively, in one embodiment of the invention, allogeneic cells may be used having matching histocompatibility to the mammalian host. To describe in further detail, the histocompatibility of the donor and the patient are determined so that histocompatible cells are administered to the mammalian host.

Unexpectedly, the doubling time of the cytokine treated cells was decreased compared with the untreated cells. See FIG. 2. The life span of the treated cells also increased. The treated cells survived longer and doubling time quicker than the untreated cells. The treated cells proliferated for more than 8 passages in collagen coated and uncoated flasks; however growth of the non-treated cells stopped at passage 7 (p7) in non-collagen coated flasks. Regardless, the collagen coated flasks containing cells treated with FGF-TGF-beta1 showed strongest growth. There was no sign of the cells slowing down its growth even after passage 8.

After the cells were harvested from the collagen coated or non-coated flasks these cells were transferred to multiwell plates to make micromass, which were stained directly with Alcian stain.

The doubling time of the primed cell may be decreased by a factor of about 0.8 to about 0.2; from about 0.7 to about 0.3; from about 0.6 to about 0.4; or about 0.5. By a factor of 0.5, it is meant that the doubling time of the cells incubated with cytokine is twice as fast as unincubated control cells.

In this regard, cytokines such as TGF-beta1 alone, TGF-beta3 alone, BMP2 and insulin or BMP2-insulin and T3 together or FGF-TGF-beta1 combination result in significant decrease in doubling time for the primed cells. Collagen coated and collagen uncoated flasks also provide significant differential results for certain cytokine incubation. See FIG. 2.

Mixed Cell Alternative Therapy

The present invention also encompasses administering a mixture of cells to a site in need thereof in a mammal to produce collagen or hyaline cartilage, wherein a first population of cells is transfected or transduced with a gene of interest to be expressed at the site of interest in a mammal. As somatic gene therapy is attempted, the present invention provides for including a second population of cells that are primed cells, which are not transfected or transduced with the gene of interest, and which cells are endogenously decreased at the wounded or diseased or otherwise debilitated site of interest.

In particular, in the mixed cell therapy approach using primed cells, the present invention discloses ex vivo and in vivo techniques for delivery of a DNA sequence of interest to the connective tissue cells of the mammalian host. The ex vivo technique involves culture of target connective tissue cells, in vitro transfection or transduction of the DNA sequence, DNA vector or other delivery vehicle of interest into the connective tissue cells, followed by transplantation of the modified connective tissue cells to the target joint of the mammalian host, so as to effect in vivo expression of the gene product of interest.

It is to be understood that while it is possible that substances such as a scaffolding or a framework as well as various extraneous tissues may be implanted together in the gene therapy protocol of the present invention, it is also possible that such scaffolding or tissue not be included in the injection system of the invention. In a preferred embodiment, in a cell-mediated gene therapy or somatic cell therapy, the invention is directed to a simple method of injecting a population of transfected or transduced connective tissue cells to the joint space so that the exogenous TGF superfamily protein is expressed in the joint space.

One ex vivo method of treating a connective tissue disorder using the mixed cell approach using primed cells, disclosed throughout this specification comprises initially generating a recombinant viral or plasmid vector which contains a DNA sequence encoding a protein or biologically active fragment thereof. This recombinant vector is then used to infect or transfect a population of in vitro cultured connective tissue cells, resulting in a population of connective tissue cells containing the vector. These connective tissue cells are then transplanted to a target joint space of a mammalian host either as a mixture with primed connective tissue cells or separately into the joint space so as to cause a mixture inside the joint, thus effecting subsequent expression of the protein or protein fragment within the joint space. Expression of this DNA sequence of interest is useful in substantially reducing at least one deleterious joint pathology associated with a connective tissue disorder.

In the mixed cell approach, in the case of the gene transfected cells, the inventive method includes employing as the gene a gene capable of encoding a member of the transforming growth factor β superfamily, or a biologically active derivative or fragment thereof and a selectable marker, or a biologically active derivative or fragment thereof.

A further embodiment of the present invention includes employing as the gene a gene capable of encoding at least one member of the transforming growth factor β superfamily or a biologically active derivative or fragment thereof, and employing as the vector any DNA plasmid vector known to one of ordinary skill in the art capable of stable maintenance within the targeted cell or tissue upon delivery, regardless of the method of delivery utilized.

Another embodiment of this invention provides a method for introducing at least one gene encoding a product into at least one cell of a connective tissue for use in treating the mammalian host. This method includes employing non-viral means for introducing the gene coding for the product into the connective tissue cell. More specifically, this method includes a liposome encapsulation, calcium phosphate coprecipitation, electroporation, or DEAE-dextran mediation, and includes employing as the gene a gene capable of encoding a member of transforming growth factor superfamily or biologically active derivative or fragment thereof, and a selectable marker, or biologically active derivative or fragment thereof.

Another embodiment of this invention provides an additional method for introducing at least one gene encoding a product into at least one cell of a connective tissue for use in treating the mammalian host. This additional method includes employing the biologic means of utilizing a virus to deliver the DNA vector molecule to the target cell or tissue. Preferably, the virus is a pseudo-virus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue.

Another preferred method of the present invention involves direct in vivo delivery of a TGF-β superfamily gene to the connective tissue of a mammalian host together with the primed cells through use of either a retroviral vector, adenovirus vector, adeno-associated virus (AAV) vector or herpes-simplex virus (HSV) vector. In other words, a DNA sequence of interest encoding a functional TGF-β or BMP protein or protein fragment is subcloned into the respective viral vector. The TGF-β or BMP containing recombinant virus is then grown to adequate titer and directed into the joint space, preferably by intra-articular injection.

Methods of presenting the DNA molecule to the target connective tissue of the joint includes, but is not limited to, encapsulation of the DNA molecule into cationic liposomes, subcloning the DNA sequence of interest in a retroviral or plasmid vector, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the connective tissue.

In a preferred embodiment, non-primed fibroblasts and chondrocytes are cultured in vitro for subsequent utilization as a delivery system for gene therapy together with the primed cells. It will be apparent that Applicants are not limited to the use of the specific connective tissue disclosed. It would be possible to utilize other tissue sources for in vitro culture techniques. The method of using the gene or cytokine of this invention may be employed both prophylactically and in the therapeutic treatment of osteoarthritis and wound healing. It will also be apparent that the invention is not limited to prophylactic or therapeutic applications for treating only the knee joint. It would be possible to utilize the present invention either prophylactically or therapeutically to treat osteoarthritis in any susceptible joint or any damage resulting from an injury caused by a tear or degradation of the cartilage.

In a further embodiment of this invention the primed cells are stored before administration to the joint space. Further, the transfected or transduced cells alone may be stored, or the mixture may be stored, but not necessarily simultaneously. In addition, the duration of storage need not be for the same time period. Thus, the individually stored cells may be mixed prior to injection. Alternatively, the cells may be stored and injected separately to form a mixture of cells within the joint space. It will be appreciated by those skilled in the art that these cells may be stored frozen in a cryo-preservative such as but not limited to a composition of about 10 percent DMSO in liquid nitrogen or an equivalent storage medium.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of proteins to joints provides direct access to a joint. However, most of the injected drugs in the form of encapsulated proteins have a short intra-articular half-life. The present invention solves these problems by introducing into the connective tissue of a mammalian host primed cells, which may include chondrocytes or fibroblasts and/or genes coding for proteins that may be used to treat the mammalian host. Genes coding for proteins with anti-arthritic properties may be used.

The primed cells may be used to treat osteoarthritis, a type of arthritis that is caused by the breakdown and eventual loss of the cartilage of one or more joints. If degenerative arthritis or osteoarthritis or any cartilage damage can be cured with just injection of the primed cells into the joint without including various physical apparatuses such as scaffolding or any other three-dimensional structure, the patients can be treated conveniently without major surgery.

Intervertebral Disc

The primed cells may be also used to regenerate intervertebral disc. The intervertebral discs make up one fourth of the spinal column's length. There are no discs between the Atlas (C1), Axis (C2), and Coccyx. Discs are not vascular and therefore depend on the end plates to diffuse needed nutrients. The cartilaginous layers of the end plates anchor the discs in place.

The intervertebral discs are fibrocartilaginous cushions serving as the spine's shock absorbing system, which protect the vertebrae, brain, and other structures (i.e. nerves). The discs allow some vertebral motion: extension and flexion. Individual disc movement is very limited—however considerable motion is possible when several discs combine forces.

Intervertebral discs are composed of an annulus fibrosus and a nucleus pulposus. The annulus fibrosus is a strong radial tire-like structure made up of lamellae; concentric sheets of collagen fibers connected to the vertebral end plates. The sheets are orientated at various angles. The annulus fibrosus encloses the nucleus pulposus.

Although both the annulus fibrosus and nucleus pulposus are composed of water, collagen, and proteoglycans (PGs), the amount of fluid (water and PGs) is greatest in the nucleus pulposus. PG molecules are important because they attract and retain water. The nucleus pulposus contains a hydrated gel-like matter that resists compression. The amount of water in the nucleus varies throughout the day depending on activity. As people age, the nucleus pulposus begins to dehydrate, which limits its ability to absorb shock. The annulus fibrosus gets weaker with age and begins to tear. While this may not cause pain in some people, in others one or both of these may cause chronic pain.

Pain due to the inability of the dehydrating nucleus pulposus to absorb shock is called axial pain or disc space pain. One generally refers to the gradual dehydration of the nucleus pulposus as degenerative disc disease. When the annulus fibrosus tears due to an injury or the aging process, the nucleus pulposus can begin to extrude through the tear. This is called disc herniation. Near the posterior side of each disc, all along the spine, major spinal nerves extend out to different organs, tissues, extremities etc. It is very common for the herniated disc to press against these nerves (pinched nerve) causing radiating pain, numbness, tingling, and diminished strength and/or range of motion. In addition, the contact of the inner nuclear gel, which contains inflammatory proteins, with a nerve can also cause significant pain. Nerve-related pain is called radicular pain.

Herniated discs go by many names and these can mean different things to different medical professionals. A slipped disc, ruptured disc, or a bulging disc can all refer to the same medical condition. Protrusions of the disc into the adjacent vertebra are known as Schmorl's nodes.

The following examples are offered by way of illustration of the present invention, and not by way of limitation.

EXAMPLES

Example 1

Preparation of Primed Chondrocytes

Example 1.1

Cell Culture and Treatments

Cells used in this study originated from primary human chondrocytes that had been cultured for an extended period in vitro. These cells have assumed a morphology and phenotype that is characteristic of fibroblasts despite their origin. Experiments were performed with cultures approximately at passage seven. Cells were seeded in two different culture formats: monolayer, and micromass. Culture medium consisted of DMEM (Lonza) with 4.5 g/L glucose, supplemented with 10% fetal bovine serum (Lonza) and 1% L-Glutamine (Lonza). Cells were incubated in 37° C., 5% $CO_2$ environment for the duration of treatment. Cells were exposed to multiple concentrations of TGF-β1 (R&D Systems) at different time points of the culture process for several lengths of incubation time.

Example 1.2

Monolayer Culture

Chondrocytes were seeded at $5 \times 10^4$ cells/well into a 6-well collagen coated plate (BioCoat, BD Biosciences). Cells were either primed with TGF-β1 at a concentration of 100 ng/mL for a period of 6 hours prior to seeding or incubated with TGF-β1 at 1 ng/mL concentration for the duration of the study. In addition to these two treatments, a co-culture of TGF-β1 producing cells and human chondrocytes were prepared at a 1:3 ratio, seeded at $5 \times 10^4$ cells/well and similarly examined for the duration of the three week study. Cells would be harvested weekly for RNA preparation and staining.

A shorter one week study was also performed. Chondrocytes were seeded at $3 \times 10^3$ cells/cm² to each well of the collagen coated 6-well plate. Four treatment groups represented the different time points at which TGF-β1 supplementation occurs: 24 hour, 48 hour, 72 hour, and two 36 hour intervals prior to cell harvest at the end of the week long study.

Example 1.3

Micromass Culture

Cell suspensions were prepared for a seeding density of 3×10$^5$ cells/15 μL droplet. Cell droplets were placed in the center of the well of a 24-well collagen coated plate (BioCoat). Cell masses were incubated for 1.5 hours at 37° C. were replenished with 1 mL of complete medium once masses were set. Cells were primed through treatment with 10 ng/mL or 50 ng/mL of TGF-β1 for duration of 6 hours or 18 hours prior to the seeding of micromasses. In addition to these four treatment groups, two groups of chondrocytes were exposed to TGF-β1 at concentrations of 1 ng/mL or 10 ng/mL for the duration of the study. The final experimental group consisted of the 3:1 ratio of TGF-β1 producing cells to untreated chondrocytes. Masses were cultured for up to four weeks.

Example 1.4

Alcian Blue Staining

Alcian blue (AB), also called Alcian blue 8GX, Ingrain blue 1, and C.I. 74240, is a phthalocyanine dye that contains copper. The dye stains acid mucopolysaccharides and glycosaminoglycans, for which it is one of the most widely used cationic dyes; the stained parts are blue to bluish-green. It can be combined with H&E staining and van Gieson staining methods. It bonds by electrostatic forces with the negatively charged macromolecules. Gradual increases in the electrolyte concentration used to wash the bound dye selectively identifies neutral, sulphated, and phosphated mucopolysaccharides.

The Alcian Blue staining occurred in conjunction with weekly cell harvests to determine the level of GAG accumulation during culture. All culture medium was aspirated from the well then washed two times with 4 mL PBS/well (Cellgro, Mediatech). Cultures were then fixed with 10% formalin (Sigma), 500 ul/well for 24-well plate and 800 ul/well for 6-well plate, for 15 minutes. 1 ml-2 mL of filtered Alcian Blue 8-GX (Sigma, 1.0% in 3% acetic acid pH 1.0) was added to each well and stained overnight at room temperature. Following the staining period each well was rinsed two times with 2-4 mL/well of 3% acetic acid, rinsed two times with 2-4 mL/well of PBS with complete aspiration between each wash. Cells were observed for stain intensity and cell morphology. Results are shown in FIG. 1.

Example 1.5

RT-PCR

RNA was isolated from weekly cell harvests using a phenol chloroform extraction procedure using TRIzol (Invitrogen). Isolated RNA was reverse transcribed using SuperScript™ reverse transcriptase (Invitrogen) to acquire cDNA constructs for each cell sample. Polymerase chain reaction was performed using the following primers synthesized by IDT:

```
Collagen IIα1 forward primer      (SEQ ID NO: 1)
5'-GACCTCGTGGCAGAGATGGAG-3', Collagen IIα1 reverse primer      (SEQ ID NO: 2)
5'-AACCTCTGTGACCTTTGACACCAG-3', Collagen Iα1 forward primer       (SEQ ID NO: 3)
5'-TGTGGCCCAGAAGAACTGGTACAT-3', Collagen Iα1 reverse primer       (SEQ ID NO: 4)
5'-AAAGGAGCAGAAAGGGCAGCATTG-3', Aggrecan forward primer           (SEQ ID NO: 5)
5'-TTCAGTGGCCTACCAAGTGGCATA-3', Aggrecan reverse primer           (SEQ ID NO: 6)
5'-ACATCACTGGTGGTGGTGGATTCT-3', Beta-catenin forward primer       (SEQ ID NO: 7)
5'-TGGCCATCTTTAAGTCTGGAGGCA-3', Beta-catenin reverse primer       (SEQ ID NO: 8)
5'-GATTTGCGGGACAAAGGGCAAGAT-3'
```

The following conditions were used for PCR in the thermocycler: Initial denaturation at 95° C. for 2 minutes, followed by 35 cycles of denaturation at 95° C. for 45 seconds, annealing at 62.5° C. for 1 minute, and extension at 72° C. for 1 minute. At the completion of all cycles a final extension period was programmed at 72° C. for 5 minutes. Gel electrophoresis of the final PCR product was performed against the control beta-actin to determine comparative levels of phenotypic genes for the TGF-β1 treated chondrocytes.

Example 2

Further Preparation of Primed Chondrocytes

Example 2.1

Monolayer Cell Culture

Two vials of hChonJ passage 5 (p5) chondrocytes (2×10$^6$ cells/vial) were thawed and seeded into an even number of collagen coated and non coated T-75 flasks at a cell seeding density of 5×10$^3$ cells/cm$^2$. Cells were initially cultured with complete media, DMEM (Lonza cat. no.) supplemented with 10% FBS (Lonza, cat. no. 14-507F) and 1% L-Glutamine (Lonza, cat. no. 17-605E).

Example 2.2

Cytokine Treatment

Figure 2:
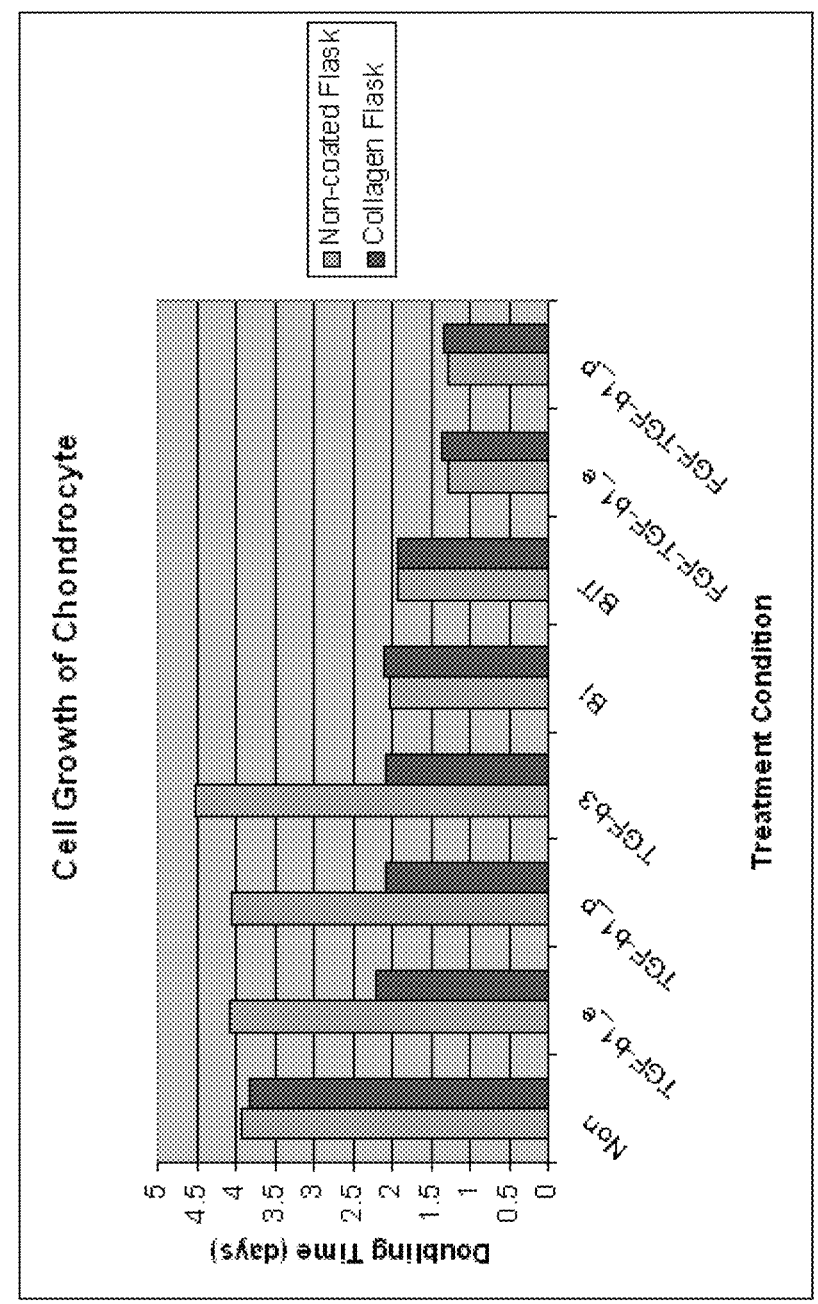
FIG. 2 shows cell growth rate in 2-dimensional culture with cytokine treatment. Cells cultured in T-75 flasks from each cytokine treatment group were harvested at confluence and counted to determine the cell growth rate from initial cell seeding numbers.

Seven different cytokine treatment groups were used in this study. 24 hours after cell seeding, the culture media in all flasks were replaced with 12 mL of cytokine supplemented media. Cytokine treatment groups (Table 1) were as follows: 50 ng/mL TGFβ1 (eBioscience or Promogen), 200 ng/mL BMP-2 (eBioscience) and 15 μg/mL Insulin (Sigma Aldrich), 200 ng/mL BMP-2 (eBioscience), 15 μg/mL Insulin (Sigma Aldrich), and 100 nM 3,3',5-Triiodo-L-thyronine (T3) (Sigma Aldrich), 10 ng/mL FGF (eBioscience) and TGFβ1 (eBioscience or Promogen), and 20 ng/mL TGFβ3 (Sigma Aldrich). Two T-75 flasks of collagen coated cells and two non coated T-75 flasks were used for negative treatment controls, 12 mL of complete DMEM. Cell culture media for each treatment group was replaced every 3-4 days. FIG. 2 also shows cell growth rate in 2-dimensional culture with cytokine treatment. Cells cultured in T-75 flasks from each cytokine treatment group were harvested at confluence and counted to determine the cell growth rate from initial cell seeding numbers.

TABLE 1

Treatment conditions for comparative cytokine study.

| Cytokine Groups | Abbreviation | Components | Concentration |
|---|---|---|---|
| TGFβ1 | TGF-b1_e | TGFβ1 | 50 ng/mL |
| TGFβ1 | TGF-b1_p | TGFβ1 | 50 ng/mL |
| BMP2 & Insulin | BI | BMP2 | 200 ng/mL |
| | | Insulin | 15 μg/mL |
| BMP2, Insulin & T3 | BIT | BMP2 | 200 ng/mL |
| | | Insulin | 15 μg/mL |
| | | T3 | 100 nM |
| FGF & TGFβ1 | FGF-TGF-b1_e | FGF | 10 ng/mL |
| | | TGFβ1 | 50 ng/mL |
| FGF & TGFβ1 | FGF-TGF-b1_p | FGF | 10 ng/mL |
| | | TGFβ1 | 50 ng/mL |
| TGFβ3 | TGF-b3 | TGFβ3 | 20 ng/mL |
| Negative Control | Ø | — | — |

Figure 5:
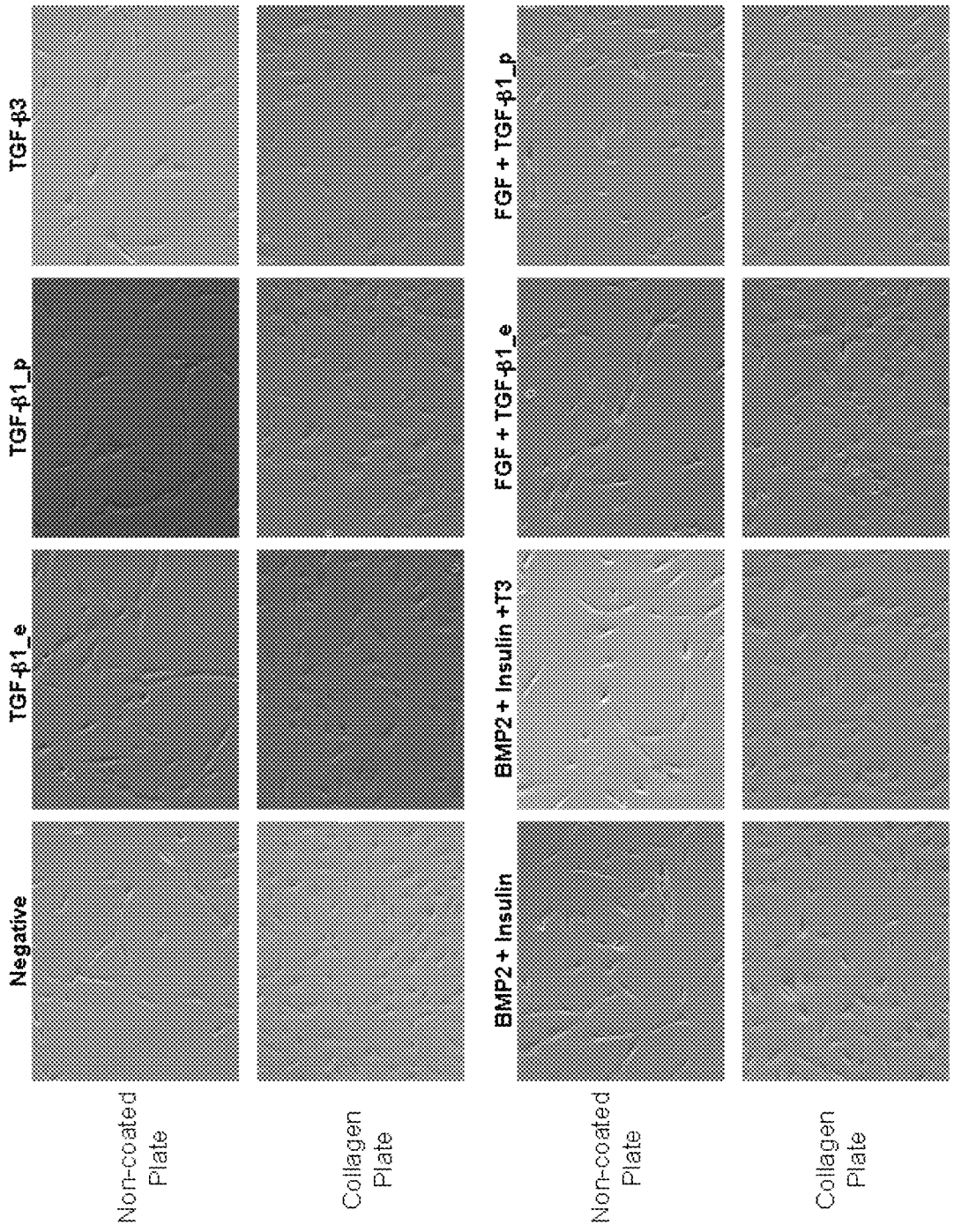
FIG. 5 shows cell morphology in 2-dimensional culture with cytokine treatment. Digital images of chondrocyte growth were taken at a time point (3 days after seeding) displaying approximately 30-50% confluence of cells. Observations in cell distribution, cell size, and morphology vary between cytokine treatment groups. Images were taken at a magnification of 100×.

FIG. 5 shows cell morphology in 2-dimensional culture with cytokine treatment. Digital images of chondrocyte growth were taken at a time point (3 days after seeding) displaying approximately 30-50% confluence of cells. Observations in cell distribution, cell size, and morphology vary between cytokine treatment groups. Images were taken at a magnification of 100×.

Figure 6:
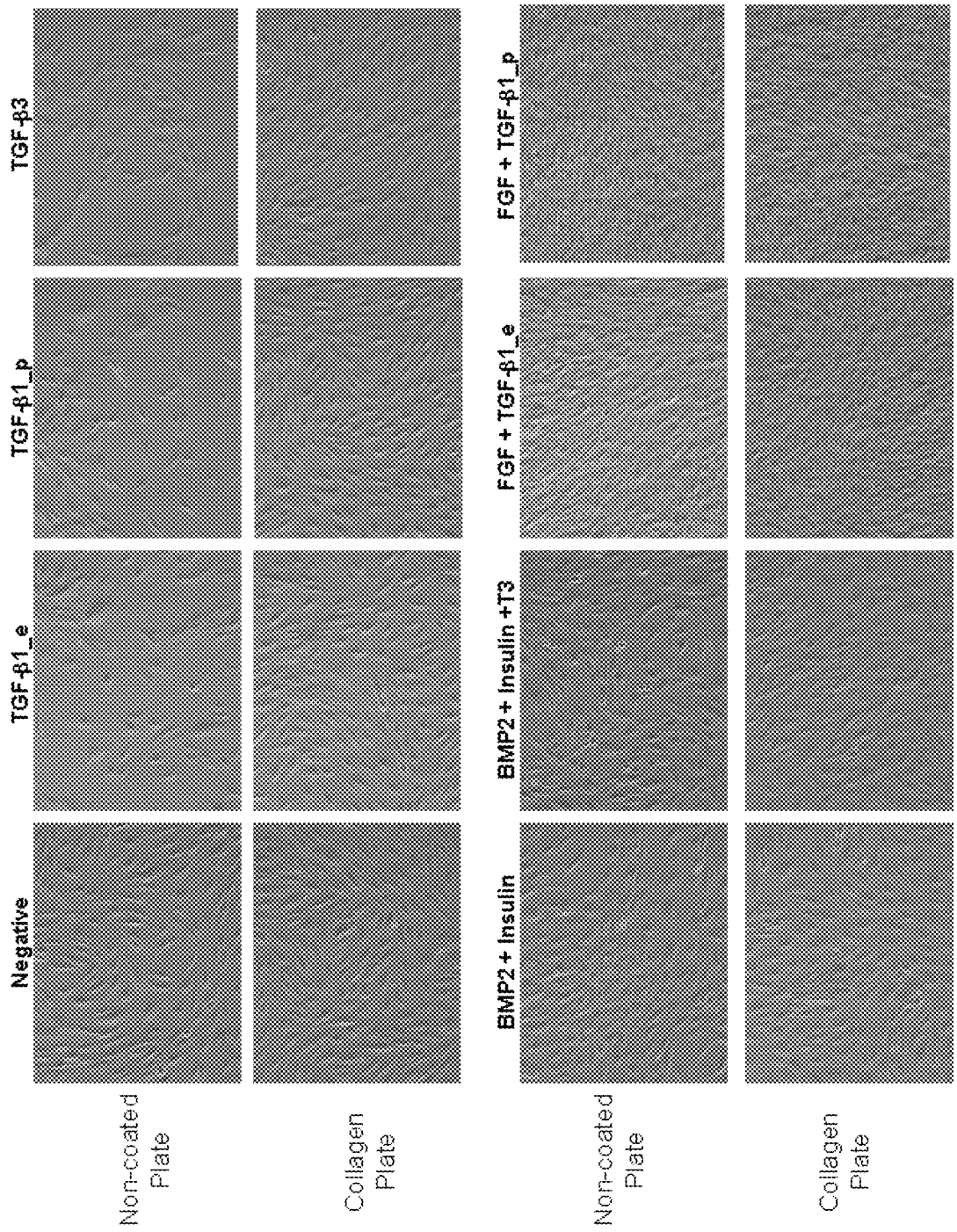
FIG. 6 shows cell morphology in 2-dimensional culture with cytokine treatment. Digital images of chondrocyte growth were taken at a time point (8 days after seeding) displaying approximately 80-100% confluence of cells just prior to the harvest of cells for RNA preparation, protein extraction, and micromass culture. Images were taken at a magnification of 100×.

FIG. 6 shows cell morphology in 2-dimensional culture with cytokine treatment. Digital images of chondrocyte growth were taken at a time point (8 days after seeding) displaying approximately 80-100% confluence of cells just prior to the harvest of cells for RNA preparation, protein extraction, and micromass culture. Images were taken at a magnification of 100×.

Example 2.3

Subculture for Second Monolayer Expansion Culture

Upon reaching confluence, a portion of the cells obtained from Example 2.2 were treated with 2 mL/flask of 1× Trypsin-Versene (EDTA) for 3-4 minutes in 37° C. Cells were checked under the microscope at 100× for confirmation of full detachment. 8 mL of complete media was added to each flask to inactivate trypsin. 30 μL of cells were removed from the total cell suspension and added to 30 μL of Trypan Blue for cell counting. After calculating the cell concentration, $2.25 \times 10^5$ cells were added to each flask for a final cell seeding density of $3 \times 10^3$ cells/cm$^2$ for the second expansion. The subcultured cells underwent the same cytokine treatment of cells as in Example 2.2 in order to confirm the effect of cytokine on the connective tissue cells in the monolayer culture obtained in Example 2.2 (data not shown).

Example 2.4

Seeding of Cell in Micromass Culture Format

A portion of cells obtained in Example 2.2 were seeded in 24 well collagen coated or non-coated culture plates according to the previous cytokine treatment scheme as set forth in Example 2.2. A set number of micromasses were allowed for each cell suspension and was determined to between 10 to 24 micromasses. $1.5 \times 10^5$ cells per micromass was calculated and that volume was removed from the cell suspension and into a fresh centrifuge tube. Cells were centrifuged at 1500 rpm, 10° C., for 7 minutes. The supernatant was aspirated and the remaining cell pellet was resuspended in complete media at a volume that allowed 20 μL/micromass. Micromasses were pipetted directly onto the naked surface of the wells at 20 μL volumes (~$1.5 \times 10^5$ cells) and incubated at 37° C., 5% $CO_2$ for approximately 1 hour. After the 1 hour incubation period 500 μL of media, cytokine conditioned or negative control complete media, was added to each well. Micromasses were cultured for 7 days before cell harvesting for RNA and protein content and Alcian Blue staining and subsequent GAG quantification.

Figure 3:
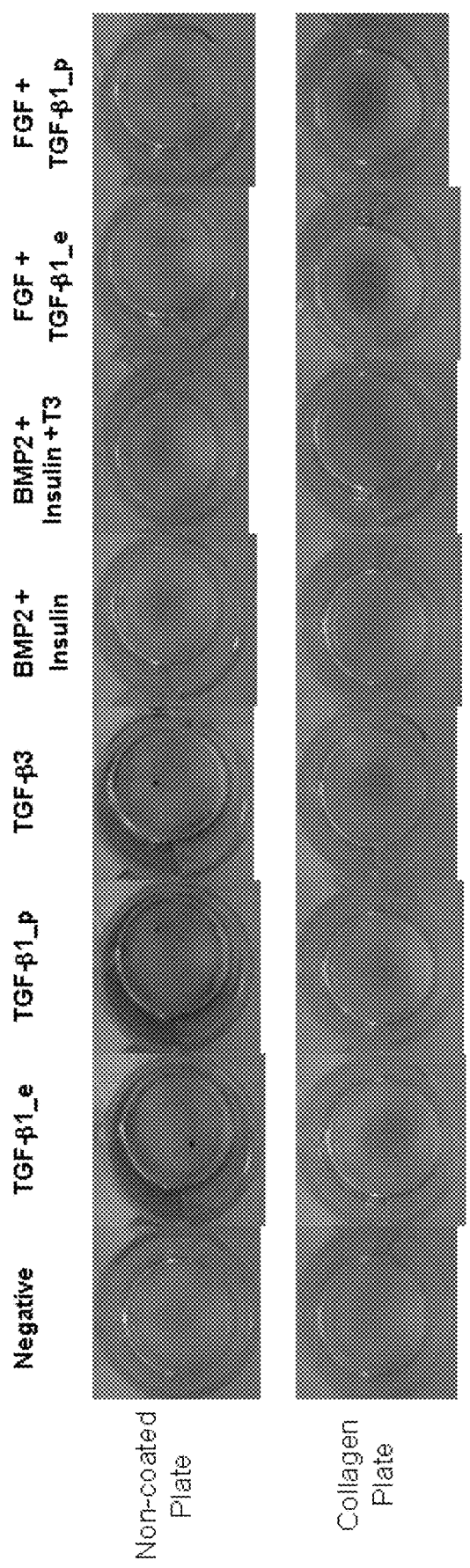
FIG. 3 shows micromass formation. Micromasses were plated at $1.5 \times 10^5$ cells/20 μl/mass directly on to the surface of culture plates without the presence of culture media. Cells were incubated for 1.5 hours for adequate cell attachment to occur and 0.5 mL/well of complete growth medium was added. Cells were cultured for a period of 7 days with one complete change of growth media at 3-4 days. At the end of the 7 day incubation period, micromasses were washed twice with 1 mL of dPBS/well and fixed with 10% formalin solution for 30 minutes. Fixing solution was removed and masses were stained with 500 uL/well of 1.0% Alcian Blue 8GX in 1N HCl overnight in 4° C. Alcian Blue staining indicates the distribution of glycosaminoglycans (GAGs) in micromass culture of chondrocytes exposed to different cytokine conditions

FIG. 3 shows micromass formation. Micromasses were plated at $1.5 \times 10^5$ cells/20 μl/mass directly on to the surface of culture plates without the presence of culture media. Cells were incubated for 1.5 hours for adequate cell attachment to occur and 0.5 mL/well of complete growth medium was added. Cells were cultured for a period of 7 days with one complete change of growth media at 3-4 days. At the end of the 7 day incubation period, micromasses were washed twice with 1 mL of dPBS/well and fixed with 10% formalin solution for 30 minutes. Fixing solution was removed and masses were stained with 500 uL/well of 1.0% Alcian Blue 8GX in 1N HCl overnight in 4° C. Alcian Blue staining indicates the distribution of glycosaminoglycans (GAGs) in micromass culture of chondrocytes exposed to different cytokine conditions.

Example 2.5

RNA Preparation and Protein Extraction of Cell Suspensions

Remaining cell suspension volumes from the cells obtained in Example 2.2 were equally divided and using the measured volume, the cell number per prep volume was calculated. Cell prep suspensions were centrifuged at 1500 rpm, 10° C., for 7 minutes. Pellets were washed with 4 mL of PBS media and centrifuged once more. The final wash volume was aspirated and cell pellets were used for RNA and protein extraction purposes. For RNA preparation a standard phenol-chloroform extraction technique was employed. For protein extraction, cells were lysed using RIPA buffer (Sigma Aldrich) and snap frozen in liquid nitrogen. RNA preparation and protein extraction and analysis was repeated using the cells from the subculture set forth in Example 2.3.

Example 2.6

RNA Preparation and Protein Extraction of Micromasses

After 1 week culture period, micromass culture plates were removed from the incubator and simultaneously processed for RNA, protein, and Alcian Blue staining. Each well was washed gently two times with 1 mL dPBS per well. Half the micromasses were set aside of RNA preparation using the standard phenol chloroform extraction. The remaining micromasses were used for protein extraction using RIPA lysis buffer and samples were snap frozen in liquid nitrogen and stored in −80° C. long term. Micromass seeding was also carried out using the subcultured cells of Example 2.3. RNA and protein extraction and analysis was also repeated using these micromasses and the results confirmed the results obtained with the micromasses seeded from the monolayer cells obtained in Example 2.2.

Example 2.7

Alcian Blue Staining 1.0% Alcian Blue-8GX stain was prepared in 1N HCL solution and filtered to remove particulate debris. 3-4 micromasses were reserved for staining purposes only. Micromasses were washed gently two times with 1 mL dPBS per well. The final wash solution was completely removed from each well. 250 µL/well of 10% formalin was added to fix each micromass and plates were incubated at room temperature for 15-30 minutes. Fixing solution was completely aspirated from each well and 500 uL/well of 1% Alcian blue-8GX stain was added and incubated overnight at 4° C. Staining solution was removed after the incubation period and micromasses were washed two times with 1 mL dPBS/well. Digital images of micromasses were taken to record the distribution of stain in each well.

Example 2.8

GAG Quantification

Figure 4:
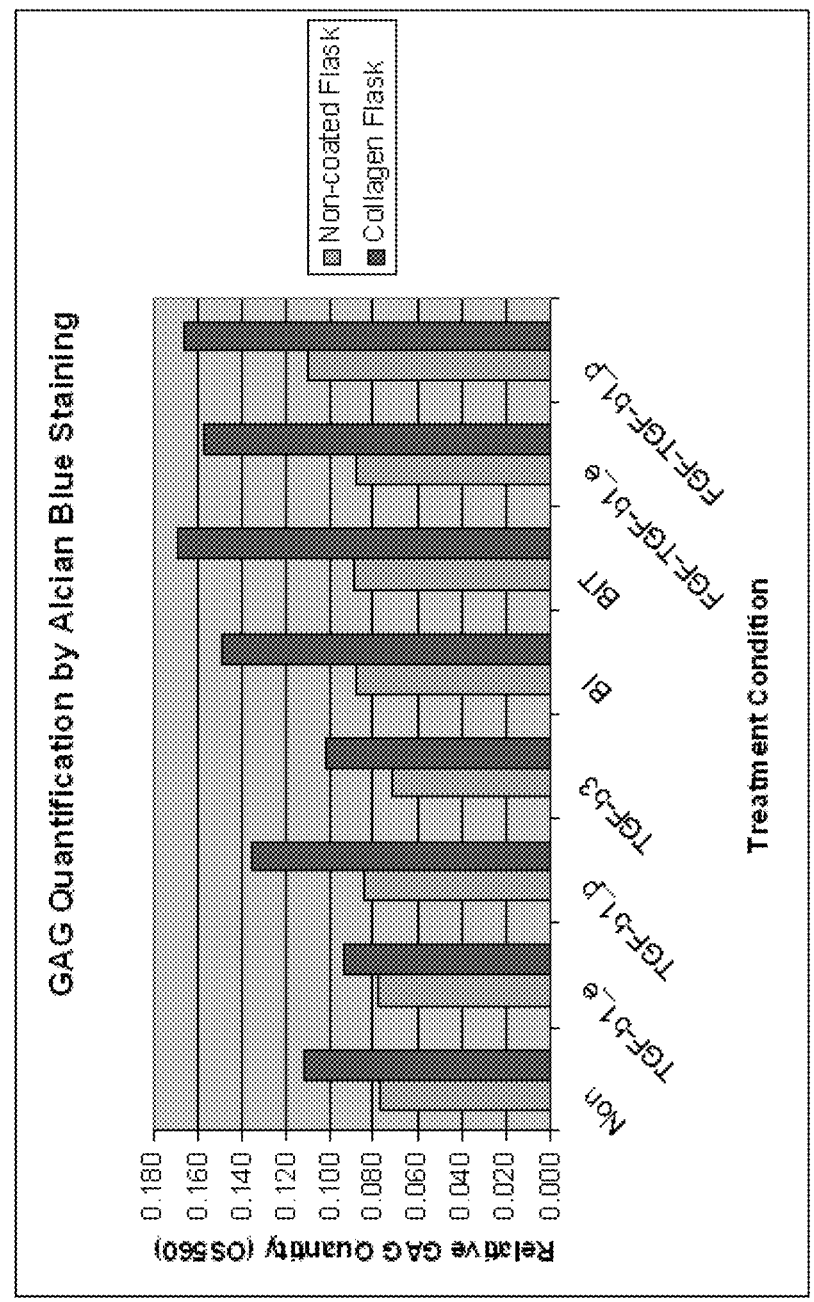
FIG. 4 shows GAG quantification of micromasses. Quantification of glycosaminoglycans can be performed through the addition of guanidine hydrochloride (Gu-HCl) which precipitates the Alcian Blue bound GAG chains of proteoglycan molecules. Alcian blue stained micromasses were incubated with 250 μl/well of 4M Gu-HCl. When most of the stain had been extracted from the micromasses, the solution was removed and the optical density was measured at 560 nm.

250 µL/well of 4M Guanidine HCl (Gu-HCl) was added and incubated for a minimum of 1 hr to 18 hr overnight in 4° C. to ensure complete extraction of stain. 100 µL of solution was removed from each well and transferred to a 96 well assay plate for observation at 560 nM. 100 uL of 4M Gu-HCl was used as a blank. FIG. 4 shows GAG quantification of micromasses. Quantification of glycosaminoglycans can be performed through the addition of guanidine hydrochloride (Gu-HCl) which precipitates the Alcian Blue bound GAG chains of proteoglycan molecules. Alcian blue stained micromasses were incubated with 250 µl/well of 4M Gu-HCl. When most of the stain had been extracted from the micromasses, the solution was removed and the optical density was measured at 560 nM.

Example 2.9

Gene Expression Analysis

Complementary DNA (cDNA) was obtained by reverse transcription of mRNA (0.5-1 µg depending on RNA concentration) using oligo dT as a primer. The reverse transcription reaction was used performed in a 20 µL, volume in a thermocycler. Expression levels of several chondrotypcier genes (Table 2) were analyzed. Gene expression analysis was carried out for both the monolayer cells and micromass cells, as well as the subcultured monolayer cells and the micromasses derived from the subcultured cells, and the results confirm each other.

TABLE 2

| \multicolumn{7}{c}{Primers used for genes of interest} |
|---|---|---|---|---|---|---|
| GOI | Product Length bp | Primer ID | Sequence (5'->3') | Length | Tm | GC % |
| Beta Actin | 838 | Beta Actin 5' | ATC TGG CAC CAC ACC TTC TAC AAT GAG CTG CG (SEQ ID NO: 9) | 32 | 76.78 | 53.12 |
| | | Beta Actin 3' | CGT CAT ACT CCT GCT TGC TGA TCC ACA TCT GC (SEQ ID NO: 10) | 32 | 76.02 | 53.12 |
| Col1a1 | 845 | Col1a1 for | TGT GGC CCA GAA GAA CTG GTA CAT (SEQ ID NO: 3) | 24 | 66.06 | 50.00 |
| | | Col1a1 rev | AAA GGA GCA GAA AGG GCA GCA TTG (SEQ ID NO: 4) | 24 | 68.61 | 50.00 |
| Col2a1 | 511 | A-Col2a1 F | CCC TGA GTG GAA GAG TGG AG (SEQ ID NO: 11) | 20 | 59.83 | 60.00 |
| | | A-Col2a1 R | GAG GCG TGA GGT CTT CTG TG (SEQ ID NO: 12) | 20 | 61.01 | 60.00 |
| Sox-9 | 310 | SOX9 for | CCC TTC AAC CTC CCA CAC TA (SEQ ID NO: 13) | 20 | 59.96 | 55.00 |
| | | SOX9 rev | TTA GGA TCA TCT CGG CCA TC (SEQ ID NO: 14) | 20 | 60.00 | 50.00 |
| ColXa1 | 288 | ColXa1 rev | GAA AAT GAC CAG GTG TGG CT (SEQ ID NO: 15) | 20 | 59.97 | 50.00 |
| | | ColXa1 rev | CGT TTT TAC GTT GCT GCT CA (SEQ ID NO: 16) | 20 | 60.05 | 45.00 |
| Aggrecan | 998 | Agg for | TGC CTC GAA ACA TCA CTG (SEQ ID NO: 17) | 20 | 59.98 | 50.00 |
| | | Agg rev | CTC TTC TAC GGG GAC AGC AG (SEQ ID NO: 18) | 20 | 60.01 | 60.00 |

Polymerase chain reaction was performed with the following conditions. After the initial denaturation at 95° C. for 2 minutes; denaturation: 95° C. for 45 seconds; annealing: 60° C. for 1 minute; and extension: 72° C. for 1 minute and 5 seconds. These steps were repeated for 35 cycles. At the end of 35 cycles, a final extension at 72° C. for 5 minutes was performed. Gel electrophoresis was conducted using 4 µL of each reaction sample with 1 µL of gel loading buffer and run on a 1.5% agarose gel at 100 V for 30 minutes. Gels are visualized under UV light to determine the presence of positive bands.

All of the references cited herein are incorporated by reference in their entirety.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A method of stimulating fibroblastic chondrocyte to gain chondrocytic characteristics in vitro comprising incubating the fibroblastic chondrocyte in a two-dimensional monolayer in a container coated with collagen with a composition consisting essentially of an active agent, which is TGF-β1 to create a primed cell, wherein the composition consists essentially of about 50 ng/ml TGF-β1.

2. The method of claim 1, further comprising TGF-β3.

3. The method of claim 1, further comprising BMP-2.

4. The method of claim 1, further comprising fibroblast growth factor (FGF).

5. The method of claim 3, further comprising insulin.

6. The method of claim 5, further comprising T3.

7. A method of stimulating regeneration of cartilage at a target site in a mammal comprising injecting a therapeutically effective amount of the primed cell obtained in claim 1 into a target joint site where cartilage is desired to be generated, wherein endogenously existing forms of the connective tissue cells are decreased at the target site, and wherein the presence of the primed cells at the target site stimulates regeneration of cartilage.

8. The method according to claim 7, wherein the subject suffers from degenerative arthritis.

9. The method according to claim 7, wherein the target site is spinal column.

10. A method of stimulating regeneration of cartilage at a target site in a mammal comprising:
incubating a fibroblastic chondrocyte in a two-dimensional monolayer in a container coated with collagen with a composition consisting essentially of an active agent, which is TGF-β1 to create a primed cell, wherein the composition consists essentially of about 50 ng/ml TGF-β1; and
injecting a therapeutically effective amount of the obtained primed cell into a target joint site where cartilage is desired to be generated, wherein endogenously existing forms of the connective tissue cells are decreased at the target site, and wherein the presence of the primed cells at the target site stimulates regeneration of cartilage.

11. The method of claim 3, wherein BMP-2 is about 200 ng/ml.

12. The method of claim 4, wherein FGF is about 10 ng/ml.

13. The method of claim 5, wherein insulin is about 15 pg/ml.

14. A method of stimulating fibroblastic chondrocyte to gain chondrocytic characteristics in vitro comprising incubating the fibroblastic chondrocyte in a two-dimensional monolayer in a container coated with collagen with a composition consisting essentially of an active agent, which is BMP-2 to create a primed cell, wherein the composition consists essentially of about 200 ng/ml BMP-2 and about 15 pg/ml insulin.

15. The method of claim 14, wherein the composition further comprises TGF-β1.

16. The method of claim 14, wherein the composition further comprises FGF.

17. The method of claim 14, wherein the composition further comprises TGF-β3.

18. A method of stimulating regeneration of cartilage at a target site in a mammal comprising injecting a therapeutically effective amount of the primed cell obtained in claim 14 into a target joint site where cartilage is desired to be generated, wherein endogenously existing forms of the connective tissue cells are decreased at the target site, and wherein the presence of the primed cells at the target site stimulates regeneration of cartilage.

19. The method according to claim 18, wherein the subject suffers from degenerative arthritis.

20. The method according to claim 18, wherein the target site is spinal column.

21. A method of stimulating regeneration of cartilage at a target site in a mammal comprising:
incubating a fibroblastic chondrocyte in a two-dimensional monolayer in a container coated with collagen with a composition consisting essentially of an active agent, which is BMP-2 to create a primed cell, wherein the composition consists essentially of about 200 ng/ml BMP-2 and about 15 pg/ml insulin; and
injecting a therapeutically effective amount of the obtained primed cell into a target joint site where cartilage is desired to be generated, wherein endogenously existing forms of the connective tissue cells are decreased at the target site, and wherein the presence of the primed cells at the target site stimulates regeneration of cartilage.

22. The method of claim 14, wherein the composition further comprises TGF-β1.

23. The method of claim 14, wherein the composition further comprises FGF.

24. The method of claim 14, wherein the composition further comprises TGF-β3.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Collagen IIalpha1 forward primer

<400> SEQUENCE: 1
gacctcgtgg cagagatgga g                                               21

<210> SEQ ID NO 2
<211> LENGTH: 24
<212> TYPE: DNA
<213> ORGANISM: Artificial Sequence
<220> FEATURE:
<223> OTHER INFORMATION: Collagen IIalpha1 reverse primer

<400> SEQUENCE: 2
aacctctgtg acctttgaca ccag                                            24

<210> SEQ ID NO 3
<211> LENGTH: 24
<212> TYPE: DNA
<213> ORGANISM: Artificial Sequence
<220> FEATURE:
<223> OTHER INFORMATION: Collagen Ialpha1 forward primer

<400> SEQUENCE: 3
tgtggcccag aagaactggt acat                                            24

<210> SEQ ID NO 4
<211> LENGTH: 24
<212> TYPE: DNA
<213> ORGANISM: Artificial Sequence
<220> FEATURE:
<223> OTHER INFORMATION: Collagen Ialpha1 reverse primer

<400> SEQUENCE: 4
aaaggagcag aaagggcagc attg                                            24

<210> SEQ ID NO 5
<211> LENGTH: 24
<212> TYPE: DNA
<213> ORGANISM: Artificial Sequence
<220> FEATURE:
<223> OTHER INFORMATION: Aggrecan forward primer

<400> SEQUENCE: 5
ttcagtggcc taccaagtgg cata                                            24

<210> SEQ ID NO 6
```

```
<211> LENGTH: 24
<212> TYPE: DNA
<213> ORGANISM: Artificial Sequence
<220> FEATURE:
<223> OTHER INFORMATION: Aggrecan reverse primer

<400> SEQUENCE: 6
acatcactgg tggtggtgga ttct                                            24

<210> SEQ ID NO 7
<211> LENGTH: 24
<212> TYPE: DNA
<213> ORGANISM: Artificial Sequence
<220> FEATURE:
<223> OTHER INFORMATION: Beta-catenin forward primer

<400> SEQUENCE: 7
tggccatctt taagtctgga ggca                                            24

<210> SEQ ID NO 8
<211> LENGTH: 24
<212> TYPE: DNA
<213> ORGANISM: Artificial Sequence
<220> FEATURE:
<223> OTHER INFORMATION: Beta-catenin reverse primer

<400> SEQUENCE: 8
gatttgcggg acaagggca agat                                             24

<210> SEQ ID NO 9
<211> LENGTH: 32
<212> TYPE: DNA
<213> ORGANISM: Artificial Sequence
<220> FEATURE:
<223> OTHER INFORMATION: Beta Actin 5'

<400> SEQUENCE: 9
atctggcacc acaccttcta caatgagctg cg                                   32

<210> SEQ ID NO 10
<211> LENGTH: 32
<212> TYPE: DNA
<213> ORGANISM: Artificial Sequence
<220> FEATURE:
<223> OTHER INFORMATION: Beta Actin 3'

<400> SEQUENCE: 10
cgtcatactc ctgcttgctg atccacatct gc                                   32

<210> SEQ ID NO 11
<211> LENGTH: 20
<212> TYPE: DNA
<213> ORGANISM: Artificial Sequence
<220> FEATURE:
<223> OTHER INFORMATION: A-Col2a1 F

<400> SEQUENCE: 11
ccctgagtgg aagagtggag                                                 20

<210> SEQ ID NO 12
<211> LENGTH: 20
<212> TYPE: DNA
<213> ORGANISM: Artificial Sequence
<220> FEATURE:
<223> OTHER INFORMATION: A-Col2a1 R

<400> SEQUENCE: 12
```

```
gaggcgtgag gtcttctgtg                                               20

<210> SEQ ID NO 13
<211> LENGTH: 20
<212> TYPE: DNA
<213> ORGANISM: Artificial Sequence
<220> FEATURE:
<223> OTHER INFORMATION: SOX9 for

<400> SEQUENCE: 13
cccttcaacc tcccacacta                                               20

<210> SEQ ID NO 14
<211> LENGTH: 20
<212> TYPE: DNA
<213> ORGANISM: Artificial Sequence
<220> FEATURE:
<223> OTHER INFORMATION: SOX9 rev

<400> SEQUENCE: 14
ttaggatcat ctcggccatc                                               20

<210> SEQ ID NO 15
<211> LENGTH: 20
<212> TYPE: DNA
<213> ORGANISM: Artificial Sequence
<220> FEATURE:
<223> OTHER INFORMATION: ColXa1 for

<400> SEQUENCE: 15
gaaaatgacc aggtgtggct                                               20

<210> SEQ ID NO 16
<211> LENGTH: 20
<212> TYPE: DNA
<213> ORGANISM: Artificial Sequence
<220> FEATURE:
<223> OTHER INFORMATION: ColXa1 rev

<400> SEQUENCE: 16 cgttttacg ttgctgctca                                                20

<210> SEQ ID NO 17
<211> LENGTH: 20
<212> TYPE: DNA
<213> ORGANISM: Artificial Sequence
<220> FEATURE:
<223> OTHER INFORMATION: Agg for

<400> SEQUENCE: 17
tgcctcgaaa catcactgag                                               20

<210> SEQ ID NO 18
<211> LENGTH: 20
<212> TYPE: DNA
<213> ORGANISM: Artificial Sequence
<220> FEATURE:
<223> OTHER INFORMATION: Agg rev

<400> SEQUENCE: 18
ctcttctacg gggacagcag                                               20
```